(12) United States Patent
Byun et al.

(10) Patent No.: US 7,014,979 B2
(45) Date of Patent: *Mar. 21, 2006

(54) ORGANOMETALLIC PRECURSOR MIXTURE FOR FORMING METAL ALLOY PATTERN AND METHOD OF FORMING METAL ALLOY PATTERN USING THE SAME

(75) Inventors: Young Hun Byun, Daejun-Shi (KR); Soon Taik Hwang, Kyungki-Do (KR); Byong Ki Yun, Daejun-Shi (KR); Hae Jung Son, Kyoungki-Do (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/440,273

(22) Filed: May 19, 2003

(65) Prior Publication Data

US 2004/0005412 A1    Jan. 8, 2004

(30) Foreign Application Priority Data

Jul. 3, 2002    (KR) ..................... 10-2002-0038224

(51) Int. Cl.
  *G03F 7/00*    (2006.01)
(52) U.S. Cl. ................ 430/270.1; 427/376.1; 427/383.1; 106/1.13; 106/1.14; 106/287.11

(58) Field of Classification Search ............ 430/270.1; 427/376.1, 383.1, 286.4, 376.3; 106/1.13, 106/11.4, 287.11, 287.12, 287.13, 287.1, 106/287.29, 287.3, 287.32; 438/584, 597

See application file for complete search history.

(56) References Cited

U.S. PATENT DOCUMENTS

| | | | |
|---|---|---|---|
| 5,064,685 A | | 11/1991 | Kestenbaum et al. |
| 5,387,492 A | * | 2/1995 | McCormick et al. .... 430/270.1 |
| 5,514,728 A | * | 5/1996 | Lamanna et al. ............. 522/31 |
| 5,534,312 A | | 7/1996 | Hill et al. |
| 5,856,022 A | * | 1/1999 | McCormick et al. ....... 428/500 |
| 6,348,239 B1 | | 2/2002 | Hill et al. |

FOREIGN PATENT DOCUMENTS

| | | | |
|---|---|---|---|
| JP | 62-263973 A | | 11/1987 |
| JP | 2001-221908 A | | 8/2001 |
| JP | 2001-226765 A | | 8/2001 |
| JP | 2003215792 A | * | 7/2003 |
| WO | WO 02/40637 A2 | * | 5/2002 |

* cited by examiner

*Primary Examiner*—Amanda Walke
(74) *Attorney, Agent, or Firm*—Harness, Dickey & Pierce PLC

(57) ABSTRACT

An organometallic precursor mixture for forming a metal alloy pattern and a method of forming the metal alloy pattern using the same, wherein the metal alloy pattern having improved adhesive force to a substrate, heat resistance, and resistance to atmospheric corrosion can be readily formed using the organometallic precursor mixture by and exposing step without using a separate photosensitive resin.

12 Claims, No Drawings

ORGANOMETALLIC PRECURSOR MIXTURE FOR FORMING METAL ALLOY PATTERN AND METHOD OF FORMING METAL ALLOY PATTERN USING THE SAME

BACKGROUND OF THE INVENTION

This non-provisional application claims priority under 35 U.S.C. § 119(a) on Patent Application No. 2002-38224 in KOREA on Jul. 3, 2002, which is herein incorporated by reference.

FIELD OF THE INVENTION

The present invention relates to an organometallic precursor mixture for forming a metal alloy pattern and a method of forming a metal alloy pattern using the same. More particularly, the present invention relates to an organometallic precursor mixture for forming a micro- or a nano-sized metal alloy pattern using light and without using a photosensitive resin and a method of forming such a metal alloy pattern using the same.

DESCRIPTION OF THE PRIOR ART

As well known to those skilled in the art, a patterned thin film formed on a substrate using materials having different electrical properties have been applied to various electronic devices. In an electronic device production process, a thin metal film is generally coated on a substrate such as a crystallized silicone wafer and patterned.

A conventional method of forming a metal pattern comprises the steps of depositing an organometallic compound on a silicone or glass substrate according to a chemical vapor deposition process or an atomic layer deposition process to form a thin film on the substrate; coating a photoresist on the resulting organometallic film according to a spin coating process; patterning the resulting photoresist film according to a photolithography process; and etching the patterned photoresist film. Another conventional method of forming a metal pattern comprises the steps of depositing a metal film on a substrate according to a plasma deposition process, a sputtering process, or an electric plating process; coating a photoresist on the resulting metal film; patterning the photoresist film using light; and etching the patterned photoresist film to reveal a desired metal pattern. Unfortunately, these conventional methods require the setting of high temperature and vacuum conditions, and essentially involve a patterning step using a photoresist and an etching step for removing the photoresist, thus having the disadvantage of a high production cost due to such a complicated process. Other disadvantages of these conventional methods are that resolution of the resulting pattern is inevitably reduced because the patterning and etching steps are typically repeated several times. Also, the surface of a deposited metal film is not smooth, causing these conventional methods to additionally require a flatting step.

Meanwhile, various methods of forming a metal pattern without using a photoreaction have been suggested. For example, Japanese Patent Publication No. 62-263973 discloses a method of forming a metal pattern, in which an electronic beam is irradiated to a thin film of an organometallic compound without inducing any photoreaction. In addition, U.S. Pat. No. 5,064,685 discloses a method of forming a metal thin film using a thermal decomposition reaction, comprising the steps of coating an organometallic compound-containing ink on a substrate; and heating the resulting substrate with the use of a laser beam. According to this patent, the substrate is exposed to a high temperature, and materials other than metals are prevented from being deposited on the substrate.

Another example of a method of forming a metal pattern is proposed by U.S. Pat. Nos. 5,534,312 and 6,348,239, in which organic compounds sensitive to light are coordinate-bonded to a metal to produce an organometallic compound, the organometallic compound thus produced is coated on a substrate, and the resulting substrate is irradiated by light to form a metal pattern without a coating step using a photosensitive resin. According to these patents, when the organometallic compound is coated on the substrate and exposed through a patterned mask, the light acts directly on the organometallic compound to decompose organic ligands coordinate-bonded to the metal. This results in the separation of the organic ligands from the metal, and subsequently the metal reacts with adjacent metal atoms and/or oxygen in the atmosphere to form a metal or a metal oxide pattern. However, these patents are disadvantageous in that the organometallic compound as described above is slowly decomposed by exposure to light, and so the patterning rate is slow. Other disadvantages are that ligand contamination is caused because most ligands are separated from the metal by a photoreaction, and that the oxide film thus formed is reduced and annealed under a mixed gas of hydrogen with nitrogen at 200° C. or higher for 30 minutes to several hours so as to improve conductivity of the oxide film.

Meanwhile, a metal pattern is applied to an infrared reflection film for a glass building material, a reflection plate for a reflective liquid crystal display (LCD), and a reflector layer as well as a wire in a semiconductor device, and various materials, such as Al or an Al alloy, and Ag or an Ag alloy represented by Ag—Pd, have been suggested to improve the reflexibility and functionality of the reflection film. However, Ag and Al, and alloys thereof have a shortcoming in that they are very sensitive to heat. This is due to the low heat resistance of Ag and Al by nature and the frequent occurrence of diffusion on the surface of Ag and Al at a specific temperature. As a result, for production of a reflection plate for a LCD, the processing temperature should be carefully controlled and highly limited. In addition, the infrared reflection film containing Ag or Al has poor stability against heat. For example, the infrared reflection film is discolored when it is exposed to high temperatures during the summer. In particular, Ag and Ag alloys become black ($Ag_2S$) or white (AgCl), when they are left for a long period because Ag and Ag alloys are readily oxidized, sulfurized, and chlorinated by moisture, sulfur, and chlorine in the atmosphere, thus degrading their optical properties. Moreover, the absorptivity and absorption coefficient of Ag and Ag alloy are increased at a short wavelength of 450 nm or lower to strongly reflect yellow light, thereby degrading the quality of the LCD and undesirably producing the possibility of yellowing of the LCD with time.

Even though Au in addition to Ag and Al is known as another metal having high reflexibility, Au cannot be practically used because of its very high price.

Recently, the technology of forming a reflection film with improved adhesive force, resistance to atmospheric corrosion, and heat resistance, using a binary or ternary alloy mostly consisting of Ag is suggested by Japanese Patent Laid-open Publication Nos. 2001-221908 and 2001-226765. However, this technology is not accomplished by coating an organometallic compound and photo-reacting the compound, but by sputtering or a deposition process.

SUMMARY OF THE INVENTION

The present invention has been made, keeping in mind the above disadvantages occurring in the prior art, and accordingly, an object of the present invention is to provide an organometallic precursor mixture for forming a metal alloy pattern improved in light of adhesive force, heat resistance, and resistance to atmospheric corrosion, in which ligands are readily decomposed by light to separate from metals, whereby the time for forming the metal alloy pattern is reduced.

It is another object of the present invention to provide a method of forming a metal alloy pattern using such an organometallic precursor mixture.

According to one aspect of the present invention, an organometallic precursor mixture is provided for forming a metal alloy pattern, which is produced by mixing a compound defined by the following Formula (I) with another compound defined by the following Formula (II) in a metal weight ratio of 99.99:0.01 to 80:20:

$$M_m L_n X_p \quad (I)$$

wherein,

M is a transition metal selected from the group consisting of Ag, Au, and Cu;

L is a neutral ligand selected from the group consisting of amines, phosphines, phosphites (P(OR)$_3$), phosphine oxides, arsines, and thiols; and X is an anion selected from the group consisting of halogen, hydroxide (OH$^-$), cyanide (CN$^-$), nitrite (NO$_2^-$), nitrate (NO$_3^-$), nitroxyl (NO$^-$), azide (N$_3^-$), thiocyanato, isothiocyanato, tetralkylborate, tetrahaloborate, hexafluorophosphate (PF$_6^-$), triflate (CF$_3$SO$_3^-$), tosylate (Ts$^-$), sulfate (SO$_4^{2-}$), and carbonate (CO$_3^{2-}$);

wherein m is an integer ranging from 1 to 10;

n is an integer ranging from 1 to 40; and p is an integer ranging from 0 to 10;

$$R'_a D(CH_2)_b M'(OR'')_3 \quad (II)$$

wherein,

M' is a main group element selected from the group consisting of Si, Ge, and Sn;

D is a donor atom selected from the group consisting of N, P, O, and S;

R' is a hydrogen atom, an alkyl group with 1 to 5 carbons or a functional group with 1 to 5 carbons containing N or O;

R" is a linear alkyl group with 1 to 10 carbons or a branched alkyl group with 4 to 10 carbons;

a is an integer ranging from 1 to 2; and b is an integer ranging from 0 to 5.

According to another aspect of the present invention, a method is provided of forming a metal alloy pattern, comprising the steps of dissolving the organometallic precursor mixture in a solvent to provide a coating solution; applying the coating solution to a substrate to form a thin film of the organometallic precursor on the substrate; exposing the thin film with the use of a photomask; and developing the exposed thin film to form a metal alloy or a metal alloy oxide pattern on the substrate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a method of forming a metal alloy pattern using an organometallic precursor mixture. More particularly, the metal alloy pattern is formed using the organometallic precursor mixture produced by mixing an organometallic precursor defined by the following Formula (I) with another organometallic precursor defined by the following Formula (II) in a metal weight ratio of 99.99:0.01 to 80:20:

$$M_m L_n X_p \quad (I)$$

wherein,

M is a transition metal selected from the group consisting of Ag, Au, and Cu;

L is a neutral ligand selected from the group consisting of amines, phosphines, phosphites (P(OR)$_3$), phosphine oxides, arsines, and thiols; and X is an anion selected from the group consisting of halogen, hydroxide (OH$^-$), cyanide (CN$^-$), nitrite (NO$_2^-$), nitrate (NO$_3^-$), nitroxyl (NO$^-$), azide (N$_3^-$), thiocyanato, isothiocyanato, tetralkylborate, tetrahaloborate, hexafluorophosphate (PF$_6^-$), triflate (CF$_3$SO$_3^-$), tosylate (Ts$^-$), sulfate (SO$_4^{2-}$), and carbonate (CO$_3^{2-}$);

wherein m is an integer ranging from 1 to 10;

n is an integer ranging from 1 to 40; and p is an integer ranging from 0 to 10;

$$R'_a D(CH_2)_b M'(OR'')_3 \quad (II)$$

wherein,

M' is a main group element selected from the group consisting of Si, Ge, and Sn;

D is a donor atom selected from the group consisting of N, P, O, and S;

R' is a hydrogen atom, an alkyl group with 1 to 5 carbons or a functional group with 1 to 5 carbons containing N or O;

R" is a linear alkyl group with 1 to 10 carbons or a branched alkyl group with 4 to 10 carbons;

a is an integer ranging from 1 to 2; and b is an integer ranging from 0 to 5.

An organic ligand L constituting the organometallic precursor defined by the Formula (I) is sensitive to light and so can be easily separated from a central metal and decomposed during the exposing step, thus not requiring a separate photosensitive resin-coating step as well as an etching step during the formation of a metal pattern.

The organometallic precursor defined by Formula (II) plays a roll in increasing the adhesive force of the metal alloy pattern. The organometallic precursor of the Formula (II) is used in the organometallic precursor mixture of the present invention so that M' proportion of the total metal components represented by M+M' is 0.01 to 20 wt %. When the M' content is higher than 20 wt %, specific resistance is undesirably increased and the photoreaction rate becomes slow.

According to the pattering method of the present invention, the organometallic precursor mixture is first dissolved in a solvent and then coated on a substrate to form a thin film on the substrate. Illustrative, but non-limiting examples of the substrate useful to form the pattern according to the present invention include a substrate made of an inorganic material such as a silicone or glass, a substrate made of an organic material such as a plastic, and a substrate made of a composite of the inorganic material with the organic material.

The organometallic precursor is coated on the substrate according to any of various coating processes known in the art, including, but not limited to, a spin coating process, a roll coating process, a dip coating process, a spray coating process, a flow coating process, a screen printing process, and preferably a spin coating process.

Illustrative, but non-limiting examples of the organic solvent useful to coat the organometallic precursor on the substrate include a nitrile-based solvent such as acetonitrile, propionitrile, pentanenitrile, hexanenitrile, heptanenitrile, and isobutylnitrile; an aliphatic hydrocarbon-based solvent such as hexane, heptane, octane, and dodecane; an aromatic hydrocarbon-based solvent such as anisole, mesitylene, and xylene; a ketone-based solvent such as methyl isobutyl ketone, 1-methyl-2-pyrrolidinone, cyclohexanone, and acetone; an ether-based solvent such as tetrahydrofuran, diisobutyl ether, and isopropyl ether; an acetate-based solvent such as ethyl acetate, butyl acetate, and propylene glycol methyl ether acetate; an alcohol-based solvent such as isopropyl alcohol, butyl alcohol, hexyl alcohol, and octyl alcohol; a silicone-based solvent; and a mixture thereof.

The thin film of the organometallic precursor is exposed with a photomask, and the precursor compound exposed to light is decomposed, thus differentiating a solubility of an exposed portion from that of the non-exposed portion. In other words, the exposed compound is converted into another compound different from the original compound and, in detail, when an organic ligand bonded to a metal atom is separated from the metal atom by electromagnetic radiation, the metal compound becomes more unstable to rapid decomposition into a metal or a metal oxide depending on the processing atmosphere. A photochemical reaction mechanism of the organometallic precursor of the present invention depends on the metal and the ligand. In general, however, it is surmised that a bond between the metal and the ligand is weakened according to four mechanisms, that is, a metal to ligand charge transfer mechanism, a ligand to metal charge transfer mechanism, a d—d excitation state mechanism, and an intramolecular charge transfer mechanism, thereby being completely cut to be decomposed. Ultraviolet light is most preferred as a source of light used in the electromagnetic radiation.

After the exposing step, the exposed thin film is developed with an organic solvent to produce a desired pattern. The organic solvent used in coating the substrate as described above may be used as a solvent to develop the thin film, and inorganic solvents, for example TMAH, may be also used. Examples of the organic solvent are given herein for purposes of illustration only and are not intended to limit the invention.

The resulting pattern may be additionally subjected to an oxidizing, a reducing, and/or an annealing step so as to improve its physical properties, such as the conductivity and adhesive force of the thin film. The oxidizing step is conducted in order to obtain a pure metal oxide pattern, and can be readily accomplished by reacting the pattern with an oxidizing agent. The oxidizing agent may be an organic agent including N-oxides such as trimethylamine N-oxide and pyridine N-oxide, peroxides such as bis(trimethylsilyl) peroxide, perbenzoic acid, $O_3$ and $O_2$, or may be an inorganic agent including $H_2O_2$, $H_2SO_4$ and $HNO_3$. The oxidizing condition may be varied according to the oxidizing agent to be used, although liquid- or gas-phase oxidation is typically performed. On the other hand, the reducing step is conducted in order to obtain a pure metal pattern, and can be readily accomplished by reacting the pattern with a reducing agent. Useful reductants can be exemplified by organic types, including hydrazines, silanes, amines, and derivatives thereof, as well as inorganic types, including metal hydrides such as $NaBH_4$ and $LiAlH_4$. These reductants can be used by themselves or as a solution in a suitable solvent, and can be applied to a gas- or liquid-phase reduction as needed. Meanwhile, the annealing step is conducted under a mixed gas atmosphere of $H_2/N_2$, $N_2$ gas, air or a vacuum at a temperature of 300° C. or lower, preferably 200° C. or lower. Because the organometallic precursor of the present invention can be annealed at a relatively low temperature of 300° C. or lower, unlike conventional compounds for forming a pattern, the present invention can be applied to a glass or a plastic substrate which is sensitive to heat.

Recently, most electronic devices are not composed of a single layer but rather multi-layers, and each layer may be of the same metal or different metals. According to the present invention, a procedure of forming a single layer film may be repeated to produce a multi-layered film, and the multi-layered film in which each layer consists of different metals can be formed by using various photoreactive organometallic precursors each having different central metals.

The method of forming the metal alloy pattern according to the present invention is very useful in forming a reflection plate for a reflective liquid crystal display. In addition, the method can be applied to provide a metal alloy film capable of replacing a sputter layer of a flexible display or a flat panel display, or to a CMP-free damascene process or a PR-free ITO layer forming process.

A better understanding of the present invention may be obtained in light of the following examples which are set forth to illustrate, but are not to be construed as limiting, the present invention. All compounds used herein are synthesized under a nitrogen atmosphere without moisture or oxygen in a Schlenk flask according to the Schlenk or Glove box technology.

PREPARATION EXAMPLE 1

Synthesis of $Ag(NH_2Pr)_n(NO_2)$ Compound (1) (n=1, 2, 3, and 4)

3.08 g of $AgNO_2$ (20.0 mmol) was dissolved in 15 ml of acetonitrile ($CH_3CN$) in a round Schlenk flask with a volume of 50 ml, and 3.6 g of propylamine (60.9 mmol) was then added in drops to the flask with the use of a syringe. The resulting mixture was allowed to react at a room temperature for 1 hour while agitating and filtered through a 0.2 μm membrane filter, and excess amine and solvent were removed from the filtrate under a reduced pressure to obtain a transparent yellow oil. From the analysis results, as described below, of the transparent yellow oil by a $^1H$-NMR spectrum, it can be seen that all protons resonated slightly upfiled compared to those of pure propylamine:

$^1H$-NMR($CD_3OD$, ppm): 4.87 [s, 2H, $H_2N—CH_2$]1, 2.77 [t, 2H, $N—CH_2$]], 1.61 [m, 2H, $CH_2CH_3$], 1.02 [t, 3H, $CH_2CH_3$].

PREPARATION EXAMPLE 2

Synthesis of Au(n-Butylamine)$_n$(CN) Compound (2) (n=1, 2, 3, and 4)

4.46 g of AuCN (20.0 mmol) was added to 15 ml of acetonitrile (CH$_3$CN) in a round Schlenk flask with a volume of 50 ml to form a slurry, and an excess amount of butylamine was then added in drops to the slurry with the use of a syringe until the yellow AuCN dissolved to yield a colorless solution. The solution was allowed to react at room temperature for 1 hour while agitating and filtered through a 0.2 μm membrane filter, and excess amine and solvent were removed from the filtrate under a reduced pressure to obtain a colorless solid. Meanwhile, it was confirmed that the title compound was decomposed as butylamine became slowly separated from the title compound at room temperature. From the analysis results, as described below, of the transparent yellow oil by a $^1$H-NMR spectrum, it can be seen that all protons resonated slightly upfiled compared to those of pure butylamine:

$^1$H-NMR(CD$_3$CN, ppm): 3.81 [br, 2H, H$_2$NCH$^2$-]], 2.92 [m, 2H, N—CH$_2$]], 1.60 [m, 2H, —CH$_2$CH$_2$CH$_3$]], 1.39 [m, 2H, —CH$_2$CH$_2$CH$_3$], 0.93 [s, 3H, — CH$_2$CH$_2$CH$_3$].

EXAMPLES 1 to 4

Adhesive Force Test 1.07 g of the compound (1) synthesized in preparation example 1 as a Ag precursor was mixed with various silane compounds as a Si precursor as shown in Table 1 in such a way that Si content of the resulting precursor mixture is 1.3 wt % based on the total metal content including Ag and Si. The precursor mixture was dissolved in 5 ml of acetonitrile and then coated on a glass substrate according to a spin coating process. The resulting coated film was exposed through a photomask for 10 min by use of Oriel 60200 (200W, Oriel, USA), and developed using acetonitrile to form a pattern. The pattern was reduced with a 0.05 M hydrazine solution in isopropyl alcohol, and annealed at 200° C. under vacuum for 2 min to complete the metal alloy pattern. Adhesive force of the metal alloy pattern was tested by use of an adhesive tape manufactured by 3M Co. In the case of comparative example 1, in which the pattern did not contain the silane compound, the pattern was almost exfoliate from the substrate. On the other hand, in the case of examples 1 to 4, in which the pattern contained the silane compound, the pattern was not exfoliated from the substrate. These results indicate that the pattern containing the silane compound has a very high adhesive force (see Table 1).

TABLE 1

| | Ag precursor | Si precursor | $^1$Adhesive. |
|---|---|---|---|
| Example 1 | Compound(1) | 3-aminopropyl trimethoxysilane | Pass |
| Example 2 | | 3-aminopropyl triethoxysilane | Pass |
| Example 3 | | 3-(triethoxysilyl)propyl isocyanate | Pass |
| Example 4 | | 3-glycidoxypropyl trimethoxysilane | Pass |
| Co. Ex. 1 | | — | Failure |

$^1$Adhesive. (Adhesive force): it is considered that the metal alloy pattern having the better adhesive force than a Ag film formed by a sputtering process passes an adhesive force test using an adhesive tape manufactured by 3M Co.

EXAMPLES 5 to 8

Measurement of Reflexibility

As described in following Table 2, the compound (1) or compound (2) was mixed with 3-aminopropyl trimethoxysilane in variable mixing ratios. The resulting mixture was dissolved in acetonitrile and then coated on a glass substrate according to a spin coating process. The resulting coated film was exposed for 3 min by use of Oriel 60200(200W, Oriel, USA) without using a photomask, and developed using acetonitrile to form a film containing a metal alloy. The film was reduced with a 0.05 M hydrazine solution in isopropyl alcohol to produce an almost pure metal alloy film. The procedure from the spin coating to the reduction was additionally repeated twice to yield a three-layered film. The three-layered film was annealed at 200° C. under a vacuum atmosphere to complete the metal alloy film. Adhesive force of the metal alloy film was tested by use of an adhesive tape manufactured by 3M Co., resulting in that metal alloy films of examples 5 to 8 all have better adhesive force than that of the Ag film of comparative example 2 formed using a conventional sputtering process. In addition, metal alloy films of examples 5 to 8 had the similar reflexibility to that of the Ag film of comparative example 2. From the results of a heat resistance test of the films at 200° C., furthermore, it can be seen that an agglomeration of Ag atoms was observed in the Ag film of comparative example 2, while any of the metal alloy films of examples 5 to 8 did not show this phenomenon, thus suggesting that the metal alloy film of the present invention can be applied to a multi-purpose reflection plate (see Table 2).

TABLE 2

| | Ag(Au) precursor | Si precursor | $^2$Ref. | $^3$Adh. |
|---|---|---|---|---|
| Ex. 5 | Compound 1(1.07 g) in 5 ml CH$_3$CN | 3-aminopropyl trimethoxysilane (2.6 wt % based on Ag) | 260 | Pass |
| Ex. 6 | Compound 1(1.07 g) in 5 ml CH$_3$CN | 3-aminopropyl trimethoxysilane (0.8 wt % based on Ag) | 290 | Pass |
| Ex. 7 | Compound 1(5.35 g) in 5 ml CH$_3$CN | 3-aminopropyl trimethoxysilane (0.3 wt % based on Ag) | 295 | Pass |
| Ex. 8 | Compound 2(0.74 g) in 2.5 ml CH$_3$CN | 3-aminopropyl trimethoxysilane (1.3 wt % based on Au) | 250 | Pass |
| Co. Ex. 2 | $^1$Ag film | — | 298 | Pass |

$^1$Ag film: an Ag film formed by a sputtering process
$^2$Ref. (reflexibility (%)): reflexibility of a Ag(Au)-Si film at a wavelength of 700 nm based on a Si wafer (100%)
$^3$Adh. (adhesive force): tested with the use of an adhesive tape manufactured by 3M Co.

As described above, the present invention is advantageous in that a metal alloy pattern having improved adhesive force to a substrate, heat resistance, and resistance to atmospheric corrosion can be readily formed using an inventive organometallic precursor mixture by an exposing step without using a separate photosensitive resin.

The present invention has been described in an illustrative manner, and it is to be understood that the terminology used is intended to be in the nature of description rather than of limitation. Many modifications and variations of the present invention are possible in light of the about teaching. Therefore, it is to be understood that within the scope of the appended claims, the invention may be practiced otherwise than as specifically described.

What is claimed is:

1. An organometallic precursor mixture for forming a metal alloy pattern, produced by mixing a compound defined by the following Formula (I) with another compound defined by the following Formula (II) in a metal weight ratio of 99.99:0.01 to 80:20:

$$M_m L_n X_p \tag{I}$$

wherein,
M is a transition metal selected from the group consisting of Ag, Au, and Cu;
L is a neutral ligand selected from the group consisting of amines, phosphines, phosphites, phosphine oxides, arsines, and thiols; and
X is an anion selected from the group consisting of halogen, hydroxide (OH$^-$), cyanide (CN$^-$), nitrite (NO$_2^-$), nitrate (NO$_3^-$), nitroxyl (NO$^-$), azide (N$_3^-$), thiocyanato, isothiocyanato, tetralkylborate, tetrahaloborate, hexafluorophosphate (PF$_6^-$), triflate (CF$_3$SO$_3^-$), tosylate (Ts$^-$), sulfate (SO$_4^{2-}$), and carbonate (CO$_3^{2-}$);
wherein
m is an integer ranging from 1 to 10;
n is an integer ranging from 1 to 40; and
p is an integer ranging from 0 to 10;

$$R'_a D(CH_2)_b M'(OR'')_3 \tag{II}$$

wherein,
M' is a main group element selected from the group consisting of Si, Ge, and Sn;
D is a donor atom selected from the group consisting of N, P, O, and S;
R' is a hydrogen atom, an alkyl group with 1 to 5 carbons or a functional group with 1 to 5 carbons containing N or O;
R'' is a linear alkyl group with 1 to 10 carbons or a branched alkyl group with 4 to 10 carbons;
a is an integer ranging from 1 to 2; and
b is an integer ranging from 0 to 5.

2. A method of forming a metal alloy pattern, comprising the steps of:
(a) dissolving the organometallic precursor mixture according to claim 1 in an organic solvent to provide a coating solution;
(b) applying the coating solution to a substrate to form a thin film of the organometallic precursor on the substrate;
(c) exposing the thin film with the use of a photomask; and
(d) developing the exposed thin film to form a metal alloy or a metal alloy oxide pattern on the substrate.

3. The method according to claim 2, wherein the substrate is made of a material selected from the group consisting of an inorganic material, an organic material, and a composite thereof.

4. The method according to claim 2, wherein the coating step is conducted according to a spin coating process, a roll coating process, a dip coating process, a spray coating process, a flow coating process, or a screen printing process.

5. The method according to claim 2, wherein the organic solvent is selected from the group consisting of a nitrile-based solvent, an aliphatic hydrocarbon-based solvent, an aromatic hydrocarbon-based solvent, a ketone-based solvent, an ether-based solvent, an acetate-based solvent, an alcohol-based solvent, a silicone-based solvent, and mixtures thereof.

6. The method according to claim 2, wherein the exposing step is conducted using ultraviolet light as the light source.

7. The method according to claim 2, further comprising the steps of oxidizing, reducing, and/or annealing the metal alloy or metal alloy oxide pattern after the developing step (d).

8. The method according to claim 7, wherein the annealing step is conducted under a mixed gas atmosphere of H$_2$/N$_2$, N$_2$ gas, air or a vacuum at a temperature of 300° C. or lower.

9. The method according to claim 2, wherein step (b) to the step (d) are repeated twice or more to form a multi-layered metal alloy pattern.

10. The method according to claim 9, wherein a metal substantially constituting a first metal alloy pattern layer is different from the metal substantially constituting other metal alloy pattern layers.

11. The method according to claim 7, wherein the oxidizing is performed using trimethylamine N-oxide, pyridine N-oxide, bis(trimethylsilyl) oxide, perbenzoic acid, O$_3$, O$_2$, H$_2$O$_2$, H$_2$SO$_4$ or HNO$_3$.

12. The method according to claim 7, wherein the reducing is performed using hydrazines, silanes, amines, NaBH$_4$ or LiAlH$_4$.

* * * * *